US008465442B2

(12) United States Patent
Freed

(10) Patent No.: US 8,465,442 B2
(45) Date of Patent: Jun. 18, 2013

(54) HANDLE FOR STEERABLE CATHETER

(75) Inventor: David Freed, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 798 days.

(21) Appl. No.: 10/845,595

(22) Filed: May 13, 2004

(65) Prior Publication Data

US 2005/0256375 A1   Nov. 17, 2005

(51) Int. Cl.
*A61B 5/00* (2006.01)
(52) U.S. Cl.
USPC ............................................. 600/585
(58) Field of Classification Search
USPC ............ 600/585, 101, 146, 142, 108; 604/95, 604/164, 158, 159, 95.04
See application file for complete search history.

(56) References Cited

U.S. PATENT DOCUMENTS

| 5,275,151 | A | * | 1/1994 | Shockey et al. | 600/108 |
| 5,322,064 | A | * | 6/1994 | Lundquist | 600/381 |
| 5,334,168 | A | | 8/1994 | Hemmer | |
| 5,358,479 | A | * | 10/1994 | Wilson | 604/95.04 |
| 5,423,311 | A | | 6/1995 | Snoke et al. | |
| 5,462,527 | A | * | 10/1995 | Stevens-Wright et al. | 604/528 |
| 5,507,717 | A | | 4/1996 | Kura et al. | |
| 5,846,221 | A | | 12/1998 | Snoke et al. | |
| 6,013,024 | A | | 1/2000 | Mitsuda et al. | |
| 6,458,107 | B1 | * | 10/2002 | Ockuly | 604/523 |
| 6,837,846 | B2 | * | 1/2005 | Jaffe et al. | 600/114 |
| 7,037,290 | B2 | * | 5/2006 | Gardeski et al. | 604/95.01 |
| 2003/0109861 | A1 | | 6/2003 | Shimada | |
| 2005/0215859 | A1 | * | 9/2005 | Chin et al. | 600/146 |

OTHER PUBLICATIONS

William H. Bush, Robert E. Crane, and George E. Brannon. Steerable Loop Snare for Percutaneous Retrieval of Renal Calix Calculi. AJR 142:367-368, Feb. 1984.

* cited by examiner

*Primary Examiner* — Brian Szmal
*Assistant Examiner* — Fangemonique Smith
(74) *Attorney, Agent, or Firm* — Bookoff McAndrews, PLLC

(57) ABSTRACT

A handle for controlling a steerable catheter can be aligned so that the direction of movement of the catheter is aligned with the orientation of an image on a monitor. In one embodiment, the handle is axially symmetric, allowing a physician to grasp it such that the movement of the catheter is aligned with an image displayed. In another embodiment, the handle is a grip that is rotatable with respect to the controls of a steerable catheter in order to align the movement with the image displayed.

19 Claims, 2 Drawing Sheets

HANDLE FOR STEERABLE CATHETER

FIELD OF THE INVENTION

The present invention relates to medical devices in general and to steerable imaging devices in particular.

BACKGROUND OF THE INVENTION

On most handles for a steerable imaging device, the relationship between the handle controls and the motion of the device is fixed. On some devices, however, the "up" direction as viewed on the TV monitor will probably not be the same as the "up" direction on a handle of the device. This occurs when the imaging device can rotate relative to a surrounding catheter or within the patient's body. As a result, the physician must move the controls to the left (for example) in order to steer the catheter in the "up" direction on the TV monitor. If the imaging device rotates again, the physician must re-determine which control direction corresponds to the "up" direction on the screen. This process is not only cumbersome but increases the required time to complete an examination.

SUMMARY OF THE INVENTION

To address the problems discussed above, the present invention is a handle configuration and steering mechanism that can be rotated in the user's hand such that the "up" direction on the handle can always be aligned with the "up" direction of images produced on a screen. The handle may also include a rotating collar or other device to indicate which direction on the handle corresponds to the "up" direction on the screen.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

As discussed above, the present invention is a handle that includes a steering mechanism for controlling the direction of a device to be inserted into a patient and that such device either produces images from within the body or whose position is imaged externally, such as by fluoroscopy, ultrasound, etc. The steering mechanism may be formed in a number of ways and be used with a variety of devices. In one embodiment, the steerable device is a multi-lumen catheter having one or more of the lumens dedicated to an imaging fiber and illumination fibers. The imaging and illumination fibers facilitate the transmittal of a visual image from inside the body to a physician or video camera. Alternatively, the catheter may include a solid state imaging sensor, such as a CCD or CMOS imaging chip. Another one or more of the lumens in the catheter are dedicated to pull wires that articulate the distal tip of the catheter. The pull wires have their distal ends secured at or adjacent the distal end of the catheter and their proximal ends connected to an actuator in the steering mechanism. Pulling one of the pull wires causes compression in one side of the catheter at the distal tip, which causes it to bend or articulate in that direction.

Utilizing four pull wires in four lumens allows four-way (left, right, up and down) motion. Some steerable catheters only utilize one pull wire and have only one direction of motion, while others utilize two wires for bi-directional motion. The present invention is most applicable to a four-wire system, but systems with fewer wires can also benefit.

Figure 1:
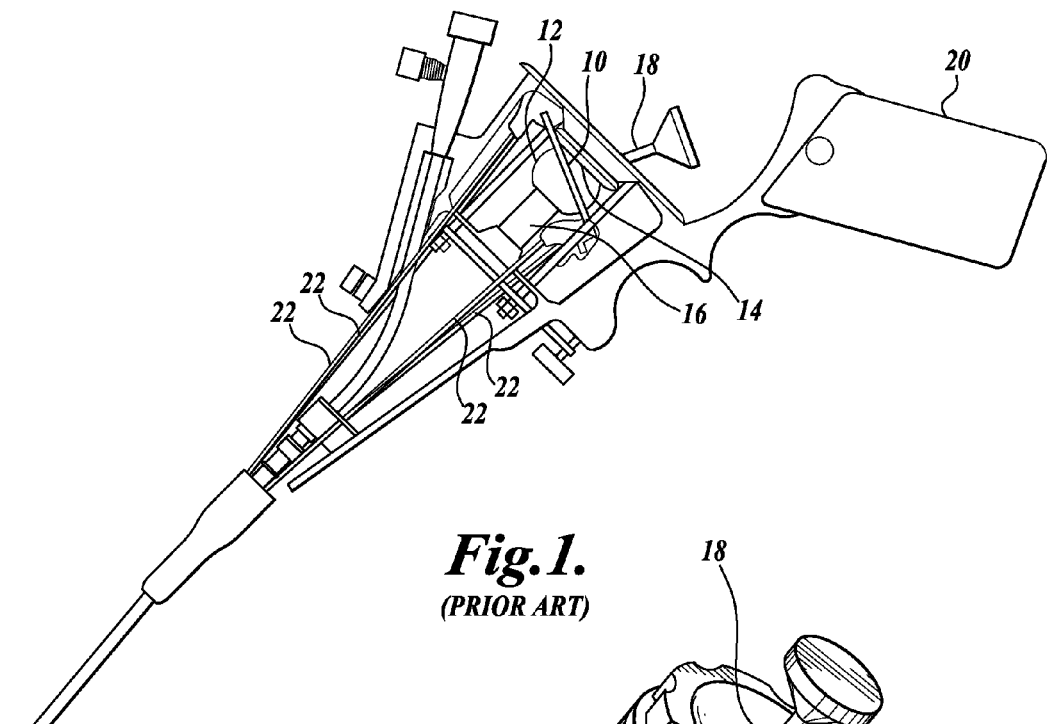
FIG. 1 illustrates a conventional 4-wire actuation handle for use in controlling the direction of a steerable catheter.

One method of actuating the pull wires is shown in FIG. 1. The steering mechanism includes a handle 20 with four pull wires 22, wherein proximal ends of the four pull wires are connected to the corners of an actuation plate 10. The steering mechanism includes a frame that supports a spherical ball and the attached actuation plate 10 so that the ball 12 can rotate between a front bearing 14 and a rear bearing 16, under direction of a lever arm 18. When the lever arm 18 is moved in a certain direction, the net result is that one or two of the four pull wires 22 are pulled. As is already known to those in the art, the resultant pull on the wires actuates the steerable tip of the catheter. This particular handle 20 is designed so that motion of the distal tip corresponds to the motion of the actuation lever—if the lever is moved down, then the distal tip of the catheter is also moved down.

The problem with the arrangement shown in FIG. 1 is that the handle 20 remains fixed with respect to the orientation of the lever arm 18. If the imaging device becomes rotated with respect to a catheter in which it is placed or the catheter is rotated with respect to a patient, movement of the lever arm in the "up" (or other) direction no longer corresponds to an "upward" (or other) movement of the image on a display. For example, the "up" direction of the visualization probe could be aligned with the "left" direction of the catheter. In this example, when the physician wants to steer the catheter towards the top of the video screen, he must actually move the control lever in a leftward direction. If the handle could be easily re-oriented such that "up" relative to the physician corresponds to "left" relative to the steering controls (which thus corresponded to "up" on the video screen), then the task of steering the tip of the catheter would be greatly simplified.

The present invention is a handle that controls a steerable catheter in a way that allows a user to easily re-orient the steering device such that movement of the pull wires in a direction produces movement of the image produced in a similar direction. Although the invention is described with respect to aligning an upward movement on a display with movement of the steering mechanism in a particular reference direction, it will be appreciated that movement in any direction can form a reference direction.

Figure 2:
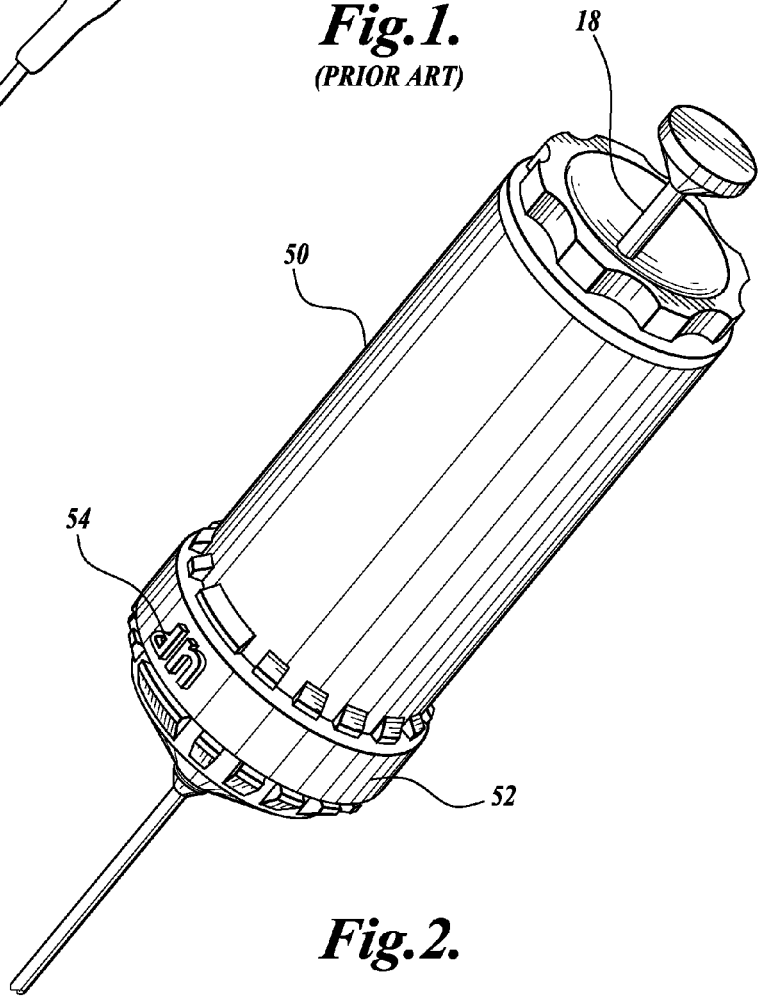
FIG. 2 is a handle for use with a steerable catheter according to an embodiment of the present invention.

As shown in FIG. 2, a handle 50 according to one embodiment of the invention contains the same lever arm 18 and catheter steering mechanism as shown in FIG. 1, but has an exterior shape that is basically symmetric about a central axis and can be held in the user's hand in any orientation. The physician can grasp the outer diameter surface of the handle 50 with the palm and fingers in a substantially vertical orientation (like a water glass), then use the thumb to operate the lever arm 18. If the physician discovers (for example) that a leftward motion of the lever arm 18 is needed to create an upward motion of the distal tip, then he could grasp the handle 50 ninety degrees clockwise so that now an upward motion of the lever arm 18 will cause an upward motion of the tip of the catheter.

The handle 50 may also include a rotatable ring 52 that can spin around the handle body, but will remain in place due to friction or other means if it is left alone. This ring 52 could include a visual marker 54 that indicates which direction is "up". Thus once the physician finds out which direction on the handle 50 corresponds to "up" on the screen, he can rotate the ring 52 such that the visual marker 54 is aligned with the "up" direction. This facilitates keeping the handle 50 aligned in the proper orientation and allows the user to put the handle down and pick it back up again without losing the proper orientation.

One particular application of the handle 50 of the present invention is for use with a fiber optic visualization catheter used in viewing the biliary tract. Such a catheter is normally introduced into the area of the biliary tract via a duodenoscope of the type well known in the art. A further improvement to the above handle would include a means for temporarily fastening the handle that actuates the catheter to the handle of the duodenoscope. Such a fastening means could include a velcro strap, a "C-clamp" and/or some kind of snap-fit component. The fastening means would allow the handle 50 to be rotated and aligned such that motion of the actuation lever could correspond with the motion of a catheter tip. The advantage of such a fastening means is that the physician can more easily operate the duodenoscope, the handle 50, and any auxiliary equipment required for the medical procedure. The physician would be able to release the catheter handle without it dropping towards the floor and without it losing rotational alignment.

Figure 3:
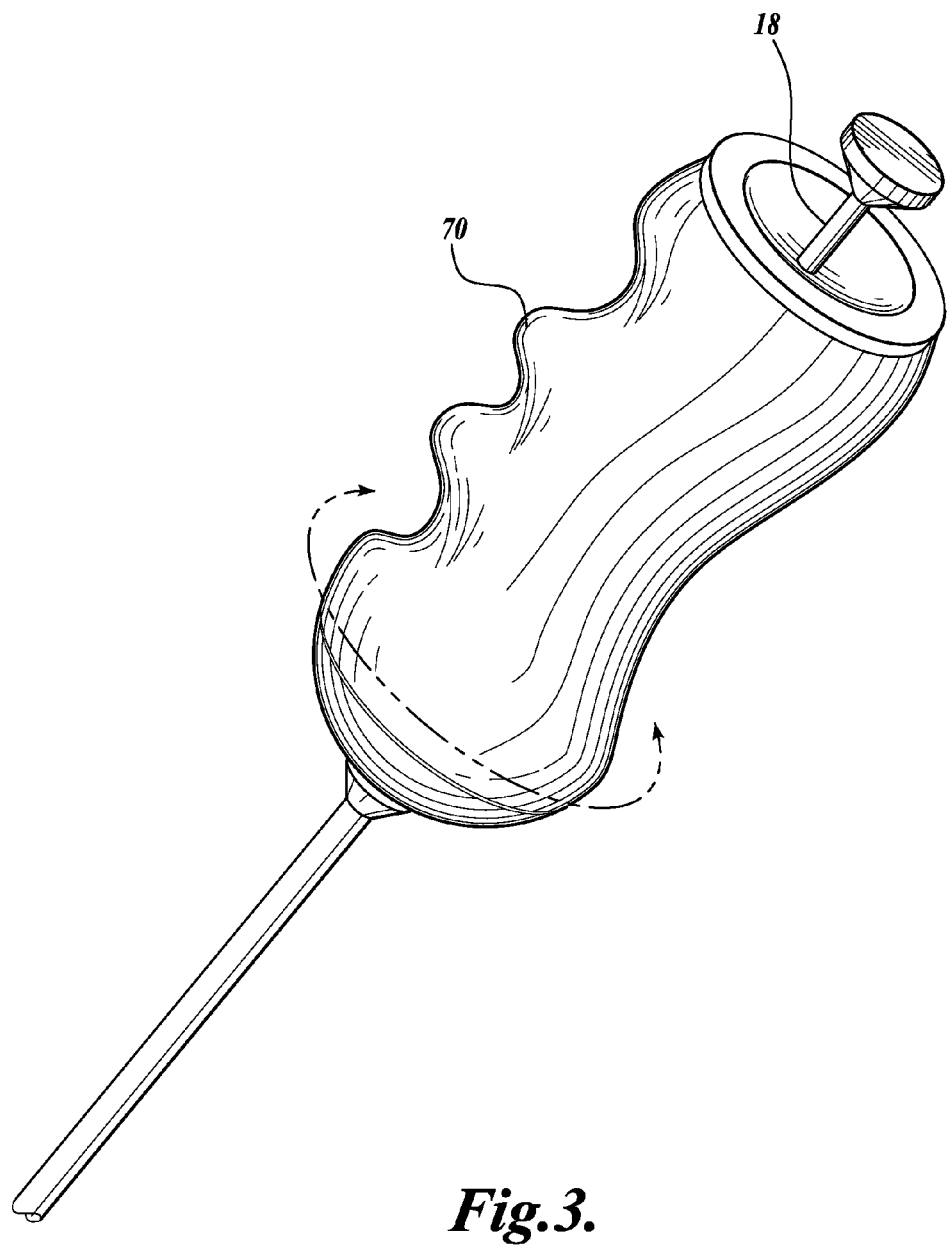
FIG. 3 is a rotatable grip for use with a steerable catheter in accordance with another embodiment of the present invention.

In another embodiment, the handle may include an ergonomically shaped exterior grip 70 as shown in FIG. 3. The grip 70 is rotatable around the steering mechanism such that a user can change the orientation of the grip 70 with respect to the lever arm 18 and associated steering mechanism. In use, the grip 70 is rotated so that movement of the lever arm 18 produces images that move in a desired direction on an image display. The grip 70 remains in its orientation by friction or may include a locking mechanism that allows the grip 70 to rotate when released.

As will be appreciated, the present invention enables the physician to always have the correct orientation between what is seen on the TV monitor and what direction to move the controls on the handle.

While the preferred embodiment of the invention has been illustrated and described, it will be appreciated that various changes can be made therein without departing from the scope of the invention. For example, the present invention can be used with any steerable device whose position is displayed on a screen. For example, catheters whose position is determined and displayed to a user using fluoroscopy or ultrasound can use the handle of the present invention in order to align movement of the catheter with a particular direction on the screen. It is therefore intended that the scope of the invention be determined from the following claims and equivalents thereof.

The embodiments of the invention in which an exclusive property or privilege is claimed are defined as follows:

1. A steerable catheter, including:
   a catheter shaft having a proximal and a distal end and one or more lumens therein, the shaft further having a longitudinal axis;
   a handle having a longitudinal axis, a proximal end, and a distal end functionally connected to the proximal end of the catheter shaft;
   a single steering lever configured to deflect the distal end of the catheter in an up direction, a down direction, a right direction, and a left direction, the single steering lever extending longitudinally from the proximal end of the handle and movably associated with the handle, the steering lever being arranged so that the orientation of the steering lever is independent of the orientation of the handle as the handle is rotated about the longitudinal axis of the handle; and
   two or more pull wires having distal ends secured at or adjacent the distal end of the catheter shaft and proximal ends secured to the steering lever, wherein movement of the steering lever causes the two or more pull wires to be selectively tensioned or released in order to deflect the distal end of the catheter shaft in a number of directions;
   wherein the handle is rotatable with respect to both the single steering lever and the catheter shaft; and
   wherein a longitudinal axis of the single steering lever, in a neutral position, is parallel with the longitudinal axis of the handle.

2. The steerable catheter of claim 1, wherein the handle is axially symmetric and surrounds the steering lever so that the user can hold the handle at any position around the steering lever.

3. The steerable catheter of claim 1, wherein the handle is ergonomically shaped.

4. The steerable catheter of claim 1, further comprising an imaging mechanism that produces images of a patient's internal body cavity.

5. The steerable catheter of claim 4, wherein the imaging mechanism includes at least one of a) fiber optic illumination and imaging bundles and b) a solid state imaging sensor.

6. A steerable device, comprising:
   an axially symmetrical handle having a proximal end and a distal end;
   a shaft having a proximal end connected to the distal end of the handle, a distal end, and one or more lumens therein, the shaft having at least one deflection position and a neutral position;
   a first pull wire having a distal end secured at or adjacent the distal end of the shaft and a proximal end; and
   a single steerable mechanism associated with the handle and connected to the proximal end of the pull wire, the steering mechanism being a lever arm that extends longitudinally and outwardly from the proximal end of the handle, wherein the lever arm has at least one actuated position that selectively tensions and/or releases the pull wire in order to deflect the distal end of the shaft to the at least one deflection position, and a neutral position that returns the distal end of the shaft to the shaft neutral position;
   wherein the orientation of the lever arm in its neutral position is independent of the orientation of the handle and the handle is rotated about its longitudinal axis;
   wherein the handle is rotatable with respect to both the lever arm and the shaft; and
   wherein a longitudinal axis of the lever arm, in its neutral position, is parallel with a longitudinal axis of the handle.

7. The steerable device of claim 6, further comprising second, third, and fourth pull wires having distal ends secured at or adjacent the distal end of the shaft and proximal ends connected to the steering mechanism for providing, in conjunction with the first pull wire, distal end deflection of the shaft in the up, down, right, and left directions.

8. A steerable device, comprising:
   a handle having a proximal end, a distal end, and a graspable section disposed between the proximal and distal ends;

a shaft having a proximal end connected to the distal end of the handle, a deflectable distal end, and one or more lumens disposed therein;

first, second, third, and fourth pull wires each having a distal end secured at or adjacent the distal end of the shaft and a proximal end, wherein movement of the first, the second, the third, and/or the fourth pull wire with respect to the shaft causes the distal end to deflect in an up direction, a down direction, a right direction, and/or a left direction, respectively; and a single steering lever movable with two degrees of freedom, the single steering lever extending longitudinally and outwardly from the proximal end of the handle and operatively connected to the proximal ends of the first, second, third, and fourth pull wires, wherein movement of the single steering lever with respect to the handle selectively tensions and/or releases the first, second, third, and/or fourth pull wires in order to deflect the distal end of the shaft, wherein a longitudinal axis of the single steering lever, in a neutral position, is parallel with a longitudinal axis of the handle;

wherein the handle comprises a grip that is rotatable with respect to the single steering lever along the longitudinal axis of the handle; and wherein the single steering lever extends from a proximal-most end of the rotatable grip.

9. The steerable device of claim 8, wherein the handle further comprises a ring that is selectively rotatable around the handle for indicating to the user the way in which the steering lever is to be activated in order to produce movement in a desired direction on a display.

10. The steerable catheter of claim 1, further comprising means for permitting the steering lever to move with two degrees of freedom.

11. The steerable catheter of claim 1, wherein the steering lever is capable of 360 degree movement.

12. The steerable device of claim 6, further comprising second, third, and fourth pull wires having distal ends secured at or adjacent the distal end of the shaft and proximal ends connected to the steering mechanism, wherein the steering mechanism is configured so that the steering lever moves with two degrees of freedom.

13. The steerable device of claim 8, wherein the longitudinal axis of the steering lever is coaxial with the longitudinal axis of the handle.

14. The steerable catheter of claim 1, wherein the catheter shaft is co-linear with the handle at the connection interface therebetween.

15. The steerable device of claim 8, wherein the two degrees of freedom includes movement in two translational directions orthogonal to each other.

16. The steerable device of claim 10, wherein the two degrees of freedom includes movement in two translational directions orthogonal to each other.

17. The steerable device of claim 12, wherein the two degrees of freedom includes movement in two translational directions orthogonal to each other.

18. The steerable catheter of claim 1, wherein the handle further comprises a ring that is selectively rotatable around the handle for indicating to the user the way in which the steering lever is to be activated in order to produce movement in a desired direction on a display.

19. The steerable device of claim 8, wherein the handle is axially symmetrical with respect to the longitudinal axis of the handle.

* * * * *

UNITED STATES PATENT AND TRADEMARK OFFICE
CERTIFICATE OF CORRECTION

| | | |
|---|---|---|
| PATENT NO. | : 8,465,442 B2 | Page 1 of 1 |
| APPLICATION NO. | : 10/845595 | |
| DATED | : June 18, 2013 | |
| INVENTOR(S) | : Freed | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 914 days.

Signed and Sealed this
Thirtieth Day of December, 2014

Michelle K. Lee
*Deputy Director of the United States Patent and Trademark Office*